United States Patent [19]

Tokuoka et al.

[11] Patent Number: 5,849,597
[45] Date of Patent: Dec. 15, 1998

[54] TREATMENT APPARATUS FOR HIGH-PRECISION ANALYSIS OF IMPURITIES IN SILICIC MATERIAL

[75] Inventors: Fumio Tokuoka; Kazuhiko Shimanuki, both of Nishi-okitamagun, Japan

[73] Assignee: Toshiba Ceramics Co., Ltd., Tokyo, Japan

[21] Appl. No.: 769,128

[22] Filed: Dec. 18, 1996

[51] Int. Cl.$^6$ ............................ G01N 1/00; G01N 33/00; B01D 00/00

[52] U.S. Cl. ........................ 436/175; 436/72; 436/182; 436/807; 422/243; 422/255; 423/324

[58] Field of Search ........................... 364/497; 422/243, 422/255, 129, 158; 73/866; 436/175, 182, 72, 807; 423/324, 336, 348

[56] References Cited

U.S. PATENT DOCUMENTS

| | | | |
|---|---|---|---|
| 4,335,438 | 6/1982 | Smolen | 364/497 |
| 5,142,920 | 9/1992 | Bart et al. | 73/866 |
| 5,582,799 | 12/1996 | Amorse et al. | 422/118 |

OTHER PUBLICATIONS

Fisher Scientific Catalog, pp. 279–280, 1983.
Fumio Tokuoka et al., Vaporphase (sublimation) decomposition method quantitative analysis of super trace impurities in a silicon bulk by ICP mass spectrometry (ETV), *Abstracts of Papers, the 55th Symposium on The Japan Society for Analytical Chemistry,* Toyama, 1984, p. 303.

*Primary Examiner*—Bradley L. Sisson
*Attorney, Agent, or Firm*—Foley & Lardner

[57] ABSTRACT

A treatment apparatus for analyzing the impurities in silicic material with high precision, includes a container having an inner space in which at least one analysis sample container and a sample decomposing solution are accommodated. The container is divided into a lid body and a lower body, each of the lid body and the lower body being opened at the division surface side thereof to form an open end and being closed at the surface side opposite to the division surface side to form a close end thereof. The inner peripheral surface of the open end of the lower body is formed in a stepwise shape so that the analysis sample container is disposed to be spaced from the surface of the decomposing solution which is stocked in the lower body, and the inner peripheral surfaces of the lid body and the lower body are smoothly continuously threadily engaged with each other through abutment faces thereof to keep the container in an appropriate hermetic level. Through the analysis process using the apparatus, the impurities contained in silicic materials used for semiconductor industries in which integration techniques are remarkably developed can be quantitatively analyzed in the order of ppt to obtain silicic products having high reliability.

13 Claims, 4 Drawing Sheets

TREATMENT APPARATUS FOR HIGH-PRECISION ANALYSIS OF IMPURITIES IN SILICIC MATERIAL

BACKGROUND OF THE INVENTION

1. Field of the Invention

The present invention relates to a treatment apparatus for highly precisely analyzing impurities contained in silicic materials. Particularly, the present invention relates to an apparatus which highly precisely analyzes impurities in high-purity required silicic materials such as silicon, quartz, silica, etc. for semiconductor manufacturing, and which can reduce external contaminants so that only the impurities in the silicic materials are left by sublimating and decomposing silicon, quartz, silica, etc. as the main component in the silicic materials to remove these components are thereby withdraw and analyze the residual impurities. According to the treatment apparatus of the present invention, impurities contained in silicic materials can be analyzed with high precision which is several tens of times higher than that of the prior art.

2. Description of Related Art

Recently, the integration of semiconductors has been enhanced, higher reliability for device characteristics has been required, and clean environments for a semiconductor manufacturing process have been established. Following such recent enhancement of the semiconductor integration, the requirement of higher reliability and the establishment of the clean environments, the analysis precision for the impurities contained in silicon wafers (monocrystal) serving as direct materials is required to be enhanced from ppb ($10^{-9}$) level to ppt ($10^{-12}$) level. Therefore, a direct testing based on electrical characteristics or the like has been insufficient to the impurity analysis, and a method of directly estimating the impurity of silicon wafers is adopted.

As a method of directly analyzing impurities in high-purity silicon have been hitherto known a neutron activation analysis method, and a method of analyzing impurities by a flameless atomic absorption method or ICP-MS method (Inductively Coupled Plasma Mass Spectrometry) after analysis samples are dissolved and decomposed with acid. These analysis methods have problems in analysis sensitivity and in contamination during a decomposition process respectively, and thus they are not directly applicable as a method of constantly analyzing the impurities in silicon wafers for semiconductor manufacturing. Of the above conventional methods, the acid dissolution method is the most popular method. The acid dissolution method is classified into a direct dissolution method and an indirect dissolution method.

According to the direct dissolution method, a sample is mixed with acid to dissolve and decompose the sample, and it is a trouble factor of this method that impurities contained in acidic reagent are left even when high-purity reagent is used. Therefore, in place of this method has been used the indirect dissolution method in which acid is vaporized and then samples are decomposed in vapor phase. The indirect dissolution method is mainly classified into a normal-pressure decomposition method and a pressure decomposition method.

According to the normal-pressure decomposition method, a decomposition process needs a long time of about 10 or more days and thus this method is not suitable for practical use. There may be used a method of decomposing a sample in pure water to shorten a decomposition time, however, this method has a problem that contamination from pure water being used may occur. On the other hand, the pressure vapor-phase decomposition method does not need a long time for the dissolution time.

FIG. 1 is a longitudinal cross-sectional diagram showing a conventional pressure vapor-phase decomposing apparatus, and FIG. 2 is a cross-sectional view which is taken along a line B—B of FIG. 1. In the conventional pressure vapor-phase decomposing apparatus shown in FIGS. 1 and 2, a lid body 11 of relatively thin polytetrafluoroethylene (PTFE) which is well known as Teflon (trade name) is brought into close contact with a container 12 having an opening portion at the upper portion thereof while both flat surface portions thereof are positionally met with each other, thereby forming a decomposition inner cylinder, and the outside of the decomposition inner cylinder is surrounded by stainless outer cylinders 20 and 21 to thereby form a space which is tightly sealed.

The pressure vapor-phase decomposition of analysis samples by using the apparatus shown in FIGS. 1 and 2 is performed substantially as follow. That is, sample decomposing solution 18 such as solution of hydrofluoric acid and nitric acid ($HF+HNO_3$) is stocked in a container 12 which is opened at the upper portion thereof (hereinafter referred to as "open container"), and sample mounting containers 16 each of which holds a sample 19 therein are mounted in the open container 12 while immersed in the solution 18. Thereafter, the system is heated up to about 100° to 200° C. from the lower surface side of the outer cylinder 21 to vaporize the sample decomposing solution 18. The vaporized sample decomposing compounds ($HF+HNO_3$) are brought into contact with the sample to sublimate silicic (Si) materials of main component in the sample as hydrofluosilic acid ($H_2SiF_6$) or silicon tetrafluoride ($SiF_4$). The sublimated $H_2SiF_6$ and $SiF_4$ are absorbed by the sample decomposing solution 18, and impurities remain in the each containers 16. This residue is analyzed to quantitatively analyze the impurities in each of the samples.

SUMMARY OF THE INVENTION

An object of the present invention is to provide an apparatus for quantitatively analyzing, with high precision, the impurities contained in silicic materials such as silicon, quartz, silica or the like for semiconductor manufacturing, to which high purity is required.

Another object of the present invention is to enables installation of the apparatus as described above into a semiconductor manufacturing process as a regular process for the quantitative analysis of the impurities contained in the silicic materials such as silicon or the like which are treated in the semiconductor manufacturing process.

In the present invention, the sample is defined as those materials which mainly contain silicic materials such as simple substances of silicon or silicon oxide used for semiconductor silicon single crystal wafers, quartz glass crucibles or boats, reactor core tubes, etc. According to the present invention, silicic products to which contamination of impurities on the order of parts per trillion (ppt) is a critical factor can be suitably processed to quantitatively analyze the impurities contained in the silicic products with high precision.

The inventors of this application have reconsidered the conventional methods for analyzing the impurities contained in silicic materials to discover a pressure vapor-phase decomposing method which can perform the analysis of impurities in a short time, and meet the object as described above. Through the reconsideration, the inventors have found out the following problems.

(i) The vapor phase for decomposing the samples while being in contact with the samples is obtained by vaporizing and gasifying the sample decomposing compounds, and thus it has no impurities even on the order of ppt. The solution (HF+HNO$_3$) which is used as decomposing solution for sample typically is sold as a high-purity product in the market like the direct decomposing method. However, it is unavoidable that the products are ordinarily contaminated with impurities on the order of ppt even if they are estimated to have high purity. In addition, in the conventional method, the sample mounting containers are immersed in the sample decomposing solution as described above, so that a part of the sample decomposing solution may go over the outer walls of the sample mounting containers and leak into the containers. Therefore, reliability of the measured content of the impurities is lost.

(ii) As described above, the pressure decomposing apparatus shown in FIGS. 1 and 2 is fabricated such that the lid body 11 of PTFE is merely brought in contact with the open container 12 at the flat portions thereof, and thus it is unavoidable that corrosive (HF+HNO$_3$) vapor leaks from the contact portions. Therefore, leak gas may corrode the stainless material of the outer cylinder. If corrosion occurs, corrosion reaction gas may invade into the inner cylinder of Teflon. Accordingly, the invading gas components or the like may be measured as a part of impurities, and thus the analysis precision is lowered.

(iii) It has been hitherto considered that a highly sealing structure must be designed in order to avoid contamination of impurities from the outside. Therefore, a double structure having a PTFE inner cylinder and a stainless outer cylinder as described above has been hitherto adopted to decompose and sublimate the sample under an extremely high sealing state. However, it has been found out that the highly sealing structure is rather an obstacle to the analysis of impurities. For example, with respect to the analysis of silicon wafers, a metal element analysis of Fe, Al, Na, K, Ca, Mg, Cu, Cr, Mn, Co, etc. is performed. The analysis method as described above may be applied to these metals because they have higher boiling points than that of Si. However, if the sealing degree of the decomposing apparatus is extremely high, reactivity between each metal and HF+HNO$_3$ under vapor phase is enhanced, and metal impurities to be measured are also sublimated as fluorides. Accordingly, there is a possibility that metals which originally exist as impurities can not be analyzed (counted).

As described above, the inventors have found out and considered the above-mentioned various problems in the pressure decomposing apparatus for analyzing the impurities of the silicic material such as silicon, etc. for semiconductor manufacturing, and have made earnest studies to obtain an apparatus which can solve the above problems and analyze the impurities in silicic material with high precision, and which can be easily installed into a semiconductor manufacturing process to quantitatively analyze the impurities in silicon wafers regularly.

According to the present invention, a treatment apparatus for analyzing the impurities in silicic material with high precision comprises (1) a container having an inner space in which at least one analysis sample container and a sample decomposing solution are accommodated, (2) wherein the container is divided into a lid body having an inner space therein and a lower body having an inner space therein, each of the lid body and the lower body being opened at the division surface side thereof to form an open end and being closed at the surface side opposite to the division surface side to form a closed end thereof, and the inner surface of the closed end of the lid body being formed in a concave shape to form a ceiling portion while the closed end of the lower body forms a bottom portion at which the sample decomposing solution can be stocked, and (3) wherein the inner peripheral surface of the open end of the lower body is formed in a stepwise shape so that the analysis sample container is disposed to be spaced from the surface of the decomposing solution which is stocked at the bottom portion, and the inner peripheral surfaces of the lid body and the lower body are smoothly continuously threadily engaged with each other through abutment faces thereof.

In the treatment apparatus according to the present invention, it is preferable from the viewpoint of analysis precision that the inner peripheral surface of the open end of the lower body is formed in a two-step shape so that the analysis sample container can be mounted on the lower step and the container is prevented from coming into contact with the sample decomposing solution.

Further, it is preferable that the lid body and the lower body are threadily engaged with each other by any one of the following manners.

(1) The peripheral wall of the open end of the lid body is cut in a stepwise shape on the inner peripheral surface thereof to have a female screw portion and an abutment top face, and the peripheral wall of the open end of the lower body is cut to have a male screw portion and an abutment seat face. The lid body and the lower body are threadily engaged with each other through the engagement between the female and male screw portions.

(2) The peripheral wall of the open end of the lid body has a male screw portion and an abutment top face on the outer peripheral surface thereof, and the peripheral wall of the open end of the lower body has a female screw portion and an abutment seat face on the inner surface thereof. The lid body and the lower body are threadily engaged with each other through the engagement between the male and female screw portions.

(3) A female screw portion is concavely formed at an intermediate portion of the peripheral wall of the open end of the lid body, and a male screw portion is convexly formed at an intermediate portion of the peripheral wall of the open end of the lower body. The lid body and the lower body are threadily engaged with each other through the engagement between the female and male screw portions.

(4) A male screw portion is convexly formed at an intermediate portion of the peripheral wall of the open end of the lid body while a female screw portion is concavely formed at an intermediate portion of the peripheral wall of the open end of the lower body. The lid body and the lower body are threadily engaged with each other through the engagement between the male and female screw portions.

Furthermore, it is preferable that when the lid body and the lower body of the present invention are threadily engaged with each other as described above, a surface roughness (Ra) based on the center line average height (JIS B 0601-1976) of each of the surface of the abutment face and the flank of the thread (screw) portion (male screw and female screw) is equal to 0.1 to 3 $\mu$m, and the threading engagement portion having a thread pitch of 1 to 3 mm is set to 10 to 70 mm.

Still furthermore, in the treatment apparatus of the present invention, it is preferable that a container comprises a lid body and a lower body which are formed of PTFE and are suitably threadily engaged with each other, and the container can be kept at pressure of 0.101 to 0.500 MPa without using a stainless outer container which has been hitherto used in the prior art.

Further, it is preferable that the analysis sample container is designed in a ring shape and plural recess portions are formed in the ring portion so that samples are set in the recess portions. It is more preferable that the inner bottom portion of each recess portion is designed to have a curved surface. Still further, it is preferable that the ring body is formed of a thick member, and the recess portions are formed by boring holes in the ring body. This is because it is convenient to handle, and the dispersion of the same level as a cleaning work can be nullified.

According to the high-precision analyzing apparatus for the impurities contained in silicic material thus constructed, the container body of the treatment apparatus is divided into two bodies of the lid body and the lower body, and the open end portions of the two bodies thus divided are designed in predetermined shapes so as to be threadily engaged with each other. In addition, the sample decomposing solution can be stocked at the bottom portion of the sealed space, and steps are formed in the container so as to be away from the surface of the decomposing solution at a predetermined interval so that the analysis sample containers are mounted on the steps. Therefore, the present invention can keep directly the advantage of the conventional pressure vapor-phase decomposing method that the analysis process can be performed in a short time, and also another advantage that the analysis sample container on which the sample is mounted can be prevented from directly coming into contact with the decomposing solution stocked at the bottom portion of the treatment apparatus, and only the vapor-phase of the decomposing solution which is vaporized by heating is allowed to come into contact with the sample to decompose and sublimate the sample. Accordingly, unlike the conventional method in which the sample containers are immersed in the decomposing solution, there is no possibility that the sample decomposing solution or the like goes over the side walls of the analysis sample containers and invades into the samples. Therefore, the content of the impurities in the silicic material can be analyzed with high precision.

When the lid body and the lower body according to the present invention are threadily engaged with each other, the surface roughness Ra based on the center line average height (JIS B 0601-1976) of each of the surface of the abutment face and the flank of the thread portion (male screw and female screw) is set to a predetermined value (0.1 to 3 $\mu$m) and the length of the thread portion having a predetermined thread pitch (1 to 3 mm) is equal to 10 to 70 mm, whereby appropriate hermeticity can be achieved. Accordingly, the decomposition time can be shortened, and the analysis precision can be enhanced. Furthermore, in the treatment apparatus of the present invention, the container comprises a lid body and a lower body which are formed of PTFE and are suitably threadily engaged with each other so that the container can be kept at pressure of 0.101 to 0.511 MPa (i,e., can be kept in a sealing state) without using a stainless outer container which has been hitherto used in the prior art. Therefore, contamination of external foreigners external into the container can be easily avoided, and the problem (iii) due to high hermeticity of the conventional method can be avoided. Further, the treatment time required for the decomposition can be shortened by the sealing state whose level is set in the range as described above, and the container of the present invention is practically usable.

Still furthermore, according to the treatment apparatus of the present invention, the ceiling portion of the lid body is designed to have a curved surface, preferably to have a spherical surface. Therefore, even when water vaporized from the sample decomposing solution such as $HF-HNO_3$ or the like is condensed to form droplets, the droplets do not adhere to the upper portion, and they are enforced to fall down along the curved surface into the analysis sample containers, thereby preventing the contamination of the samples.

Still furthermore, according to the processing apparatus of the present invention, the analysis sample container on which the samples are mounted are formed in a ring shape, and the plural recess portions are formed in the peripheral direction of the ring body, preferably at regular intervals. These recess portions are used as sample mounting portions. In addition, plural samples are brought into uniform contact with the vapor-phase of the sample decomposing solution which is uniformly convected in the container, thereby decomposing and sublimating the samples. Since the homogeneity in a single silicon wafer is also estimated as a critical factor in the semiconductor manufacturing process, plural samples must be sampled for the impurity analysis of silicon wafers in consideration of the dispersion of purity in a single wafer. Therefore, this method is suitable particularly as a purity analysis of silicic material in the semiconductor manufacturing process. Particularly, this method is preferable for a comparison analysis because an analysis can be simultaneously performed for plural wafers in the same apparatus and thus the same treatment condition can be applied to these wafers. Further, since the recess portions on which the samples are mounted are designed to have curved surfaces, the residue can be extremely easily and properly withdrawn, and thus the impurities can be quantitatively analyzed with high precision.

According to the treatment apparatus for the high-precision analysis of the impurities in silicic material, the impurities contained in the silicic materials such as silicon, quartz glass, etc. for semiconductor wafers can be measured with high precision which is several tens times higher that of the conventional method, and also quantitatively analyzed on the order of ppt or less. Accordingly, the treatment apparatus of the present invention enhances the integration of semiconductors more and more, and can be practically used as a pre-treatment for the quantitative analysis of impurities in silicic materials in the semiconductor manufacturing process which is severe to an extremely small amount of contaminants.

DETAILED DESCRIPTION OF THE PREFERRED EMBODIMENTS

Preferred embodiments according to the present invention will be described hereunder with reference to the accompanying drawings, however, the present invention is not limited to these preferred embodiments.

Figure 3:
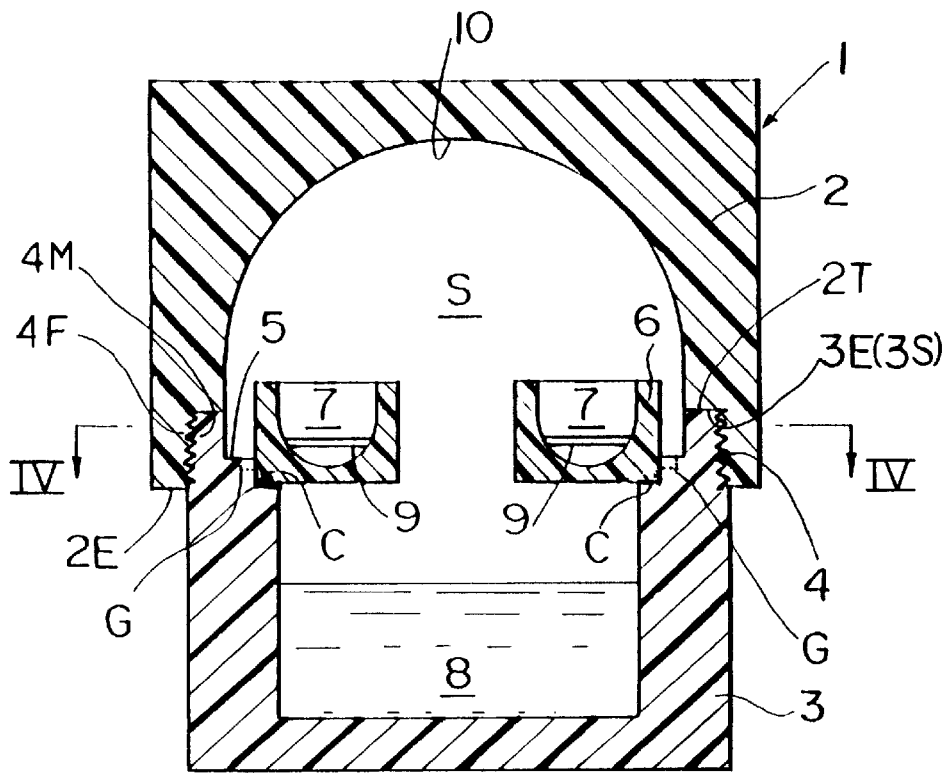
FIG. 3 is a longitudinal sectional view showing an embodiment of a sample treatment apparatus according to the present invention.
Figure 4:
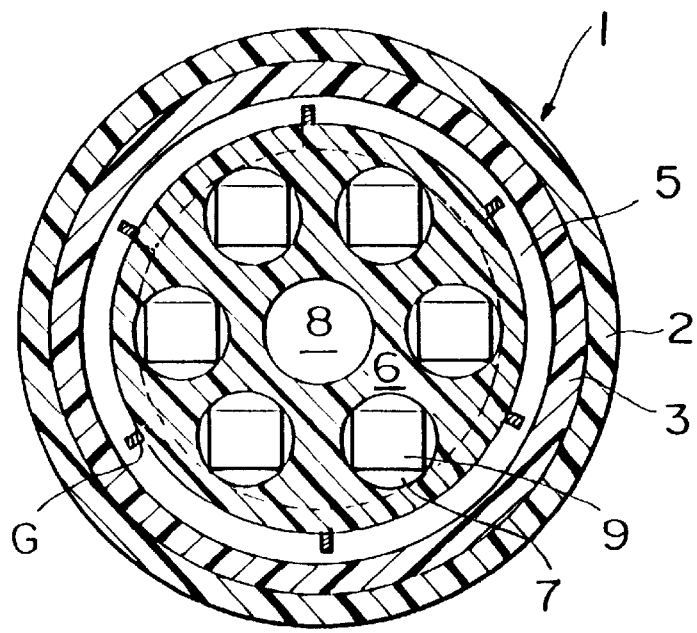
FIG. 4 is a cross-sectional view taken along a line IV—IV of FIG. 3.

FIG. 3 is a longitudinal sectional view showing an embodiment of a treatment apparatus according to the present invention, and FIG. 4 is a cross-sectional view which is taken along a line IV—IV of FIG. 3.

In FIGS. 3 and 4, a container 1 which constitutes a silicic material vapor-phase decomposing apparatus for analyzing impurities contained in silicic materials with high precision comprises a cylindrical lid body 2 and a cylindrical lower body 3. The lid body 2 and the lower body 3 are closed at one end portions thereof, and threadily engaged with each other at the open end portions thereof which are opposite to the closed end portions. That is, the container 1 is constructed as a sealed cylindrical body with a lid, and has an inner space S therein. The lid body 2 and the lower body 3 are preferably engaged with each other by threadily engaging screw portions 4 which are formed by threading the open end portions of the lid body 2 and the lower body 3.

The mode of the threading engagement it not limited to a specific one, and any mode may be used insofar as the inner space S can be kept at a sealing state ranging from 0.101 to 0.500 MPa, preferably from 0.150 to 0.2 MPa. For example, PTFE is used as a material for the container, and as shown in FIG. 3, the peripheral wall 2E of the open end of the lid body 2 is cut in a stepwise shape on the inner peripheral surface thereof to form a female screw portion 4F and an abutment top face 2T. Further, the peripheral wall 3E of the open end of the lower body 3 is cut to have a male screw portion 4M and an abutment seat face 3S. The female screw portion 4F of the lid body 2 and the male screw portion 4M of the lower body 3 thus formed are threadily engaged with each other while the respective abutment faces 2T and 3S are brought into close contact with each other.

Figure 5:
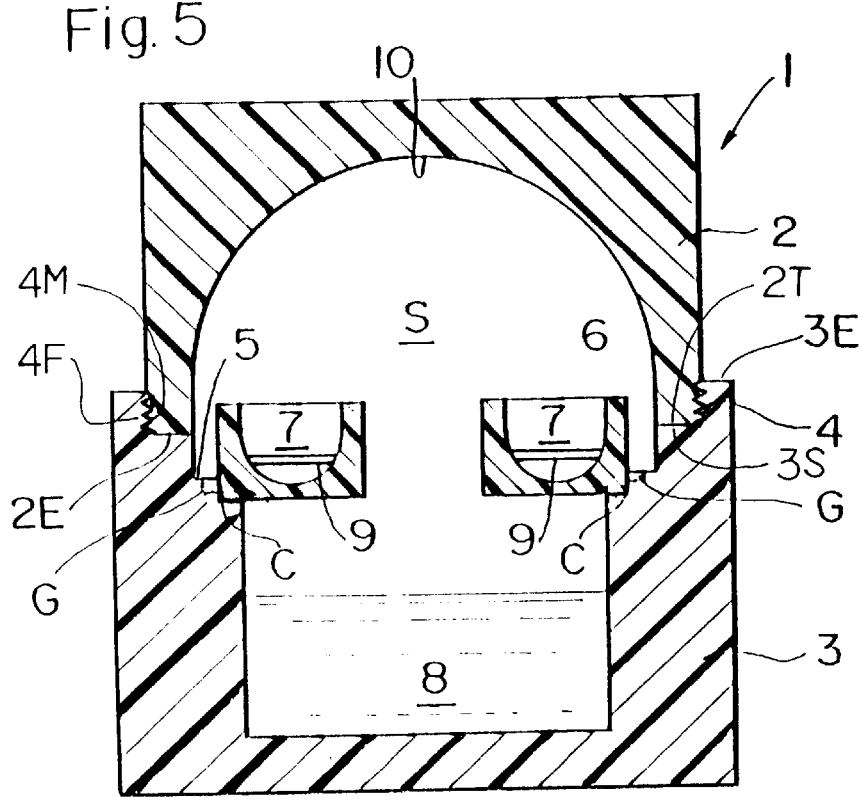
FIG. 5 is a longitudinal sectional view showing another embodiment of the sample treatment apparatus having a threading portion between a lid body and a lower body which is different from that of FIG. 3.
Figure 6:
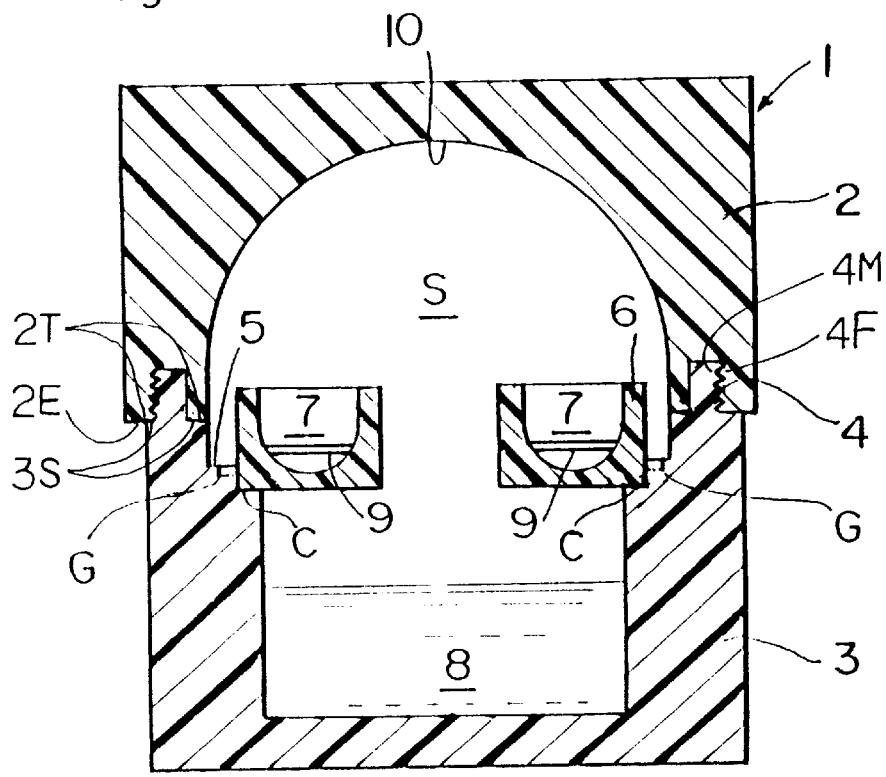
FIG. 6 is a longitudinal sectional view showing another embodiment of the sample treatment apparatus having a threading portion between a lid body and a lower body which is different from those of FIGS. 3 and 5.
Figure 7:
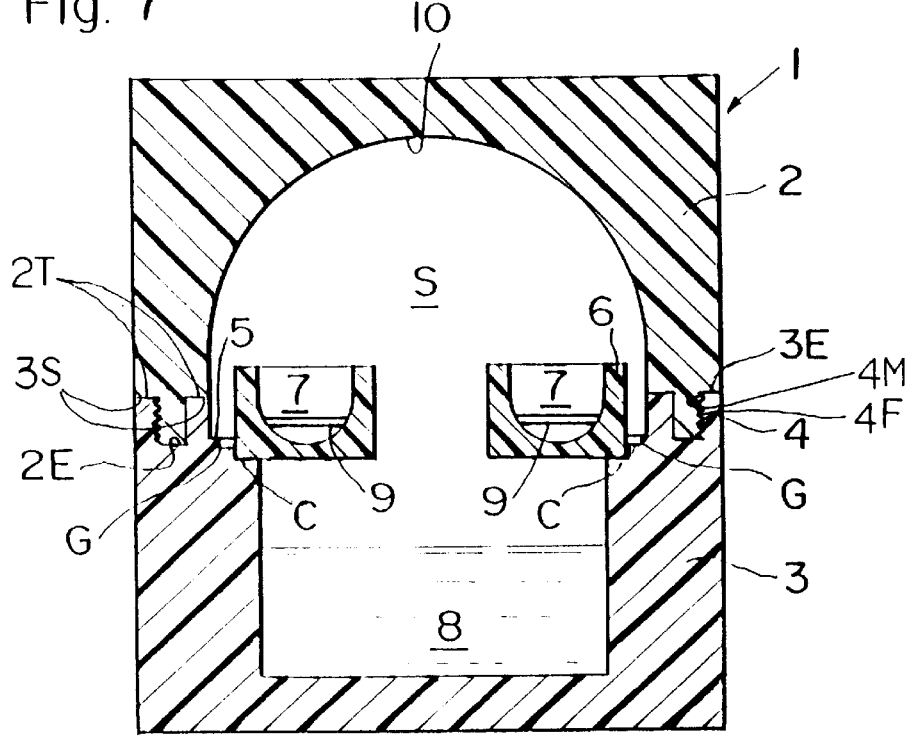
FIG. 7 is a longitudinal sectional view showing another embodiment of the sample treatment apparatus having a threading portion between a lid body and a lower body which is different from those of FIGS. 3, 5 and 6.

FIGS. 5 to 7 show other embodiments of the engagement between the lid body and the lower body.

According to an embodiment shown in FIG. 5, a male screw portion 4M and an abutment top face 2T are formed on the outer peripheral surface of the peripheral wall 2E of the open end portion of the lid body 2 while a female screw portion 4F and an abutment seat face 3S are formed on the inner surface of the peripheral wall 3E of the open end portion of the lower body 3. The lid body 2 and the lower body 3 are threadily engaged with each other while brought into close contact with each other at the abutment faces 2T and 3S thereof.

According to an embodiment shown in FIG. 6, a female screw portion 4F is concavely formed at the intermediate portion of the peripheral wall 2E of the open end portion of the lid body 2 while a male screw portion 4M is convexly formed at the intermediate portion of the peripheral wall 3E of the open end portion of the lower body 3. The lid body 2 and the lower body 3 are threadily engaged with each other through the engagement between the male and female screw portions 4M and 4F while the abutment faces 2T, 2T and 3S, 3S thereof are in close contact with each other.

According to an embodiment shown in FIG. 7, a male screw portion 4M is convexly formed at the intermediate portion of the peripheral wall 2E of the open end portion of the lid body 2 while a female screw portion 4F is concavely formed at the intermediate portion of the peripheral wall 3E of the open end portion of the lower body 3. The lid body 2 and the lower body 3 are threadily engaged with each other through the engagement between the male and female screw portions 4M and 4F while the abutment faces 2T, 2T and 3S, 3S thereof are in close contact with each other.

The lid body 2 and the lower body 3 of the container 1 is preferably formed of PTFE, and are threadily engaged with each other in the above manner. Each of the lid body 2 and the lower body 3 has an abutment face having a surface roughness (Ra) of 0.1 to 3 $\mu$m based on the center line average height (JIS B 0601-1976), and also has a thread portion which has a length of 10 to 70 mm, preferably 20 to 50 mm in the up-and-down direction of the container, that is, in a substantially vertical direction, and has a pitch of 1 to 3 mm, preferably 1.5 to 2.5 mm. The surface roughness (Ra) of the thread (screw) portion (the flank of the male screw or female screw which are formed in each of the lid body and the lower body) is preferably equal to 0.1 to 3 $\mu$m like the abutment face. The length of the thread portion at which the lid body of the container are threadily engaged with each other is set to the above range, and the surface roughness (Ra) of each of the abutment face and the thread portion is set to the above range, whereby the inner space S of the container 1 has such appropriate sealing state that it can be kept at a pressure range which is more than 0.1 MPa and is not more than 0.5 MPa as described above. Therefore, according to the present invention, volatilization of impurity such metal as fluoride which has been caused by the high hermeticity in the conventional method can be prevented, and high-precision quantitative analysis can be performed, so that the analysis precision can be enhanced. In this case, if the container 1 has a hermetic level below 0.1 MPa, about one week is required for the decomposition. On the other hand, if the container 1 has a sealing state which is higher than 0.1 MPa by 0.001 MPa, one data is required as the decomposition time. Further, if the container 1 has sealing state from 0.150 to 0.2 MPa, the decomposition is completed in several hours. Therefore, the hermetic level of the container according to the present invention is more preferable industrially. On the other hand, if the container 1 has a sealing state which is higher than 0.5 MPa, like the conventional method, the analysis precision of the impurities may be reduced, and this condition is preferred.

A step 5 is formed on the inner peripheral surface of the lower body 3 as shown in FIGS. 5, 6 and 7. The width of the step 5 may be set to any suitable value on the basis of the shape and size of an analysis sample container 6 insofar as the analysis sample container 6 can be stably mounted on the step. The position at which the step 5 is formed is not limited to a special one. However, the step 5 may be formed at a predetermined interval (height) from the surface of the sample decomposing solution 8 (HF–HNO$_3$, for example) which is stocked at the bottom portion of the lower body 3 and volatilized with heat to decompose the sample. The interval distance (height) from the surface of the sample decomposing solution to the step 5 is preferably set to about 10 mm or more. This distance can be adjusted by adjusting the amount of the sample decomposing solution to be stocked on the basis of the volume of the container 1, the amount of the sample to be analyzed and the desired amount of the sample decomposing solution. With this arrangement, the ring-shaped analysis sample container 6 mounted on the step 5 is insulated from the sample decomposing solution 8 while they are not in contact with each other in the container 1. Accordingly, the contamination of the sample decomposing solution 8 into the sample mount portions 7 can be prevented.

The width of the step 5 is set to such a value that when plural containers are independently mounted on the step 5, at least each sample container can also be mounted stably on the step 5. The mount of the analysis sample containers on the step 5 may be performed by first disposing a ring-shaped sample container mount portion on the step 5 and then disposing plural analysis sample containers on the ring-shaped sample container. In this arrangement, the step width may be set to a smaller value than the arrangement in which the plural containers are independently mounted on the step.

In place of the above-described independent arrangement of plural containers on the step, there may be used a ring-shaped analysis sample container having an unified body which comprises a sample container mount member and a sample container which is formed by suitably forming plural recess portions in a ring-shaped member so that samples are mounted on the recess portions. Particularly, a ring-shaped analysis sample container 6 having analysis sample mount portions 7 which are formed in the recess shape in a peripheral direction of the thick ring-shaped body is preferably used.

In the above-described ring-shaped analysis sample container 6 formed by integrally forming the sample container mount member and the sample containers, it is preferable that the analysis sample mount portions 7 on which the samples are mounted are formed by scooping out the bottom portion of the ring-shaped member in a curved shape such as a spherical shape or the like. When the bottom portion of the ring-shaped member is scooped out in a rectangular shape, it is difficult to perfectly withdraw residues on the rectangular analysis sample mount portions, and thus variation is liable to occur in analysis values. On the other hand, when the bottom portion is scooped out in a curved shape, the residues can be easily and sufficiently withdrawn, so that the analysis precision of the impurities can be enhanced. The diameter and depth of the recess portions of the analysis sample mount portions 7 may be suitably selected to meet the amount of the sample to be mounted thereon.

When the ring-shaped sample container mount member or the ring-shaped analysis sample container as described above is used, the ring-shaped analysis sample container 6 can be securely mounted on the step 5 by forming a notch portion C in the step 5 as shown in FIG. 3.

In the present invention, the shape of the outer body of the container 1 and the shape of the inner space S of the container 1 are not limited to the special ones, and any shape may be adopted insofar as the sample and the analysis sample decomposing solution can be accommodated in a suitable arrangement while hermetically sealed. The horizontally (laterally) sectional shape of the inner space S is not limited to the special one, and it may be a square-cornered shape (for example, angle, rectangle or the like), or a curved shape (for example, circle, ellipse or the like). It is preferable that both the outer body and the inner space S as shown in FIGS. 3 and 4 are designed in a cylindrical shape, or the inner space S is designed in a cylindrical shape (i.e., the horizontally sectional shape of the inner space S is circular) while the outer body is designed in a pillar shape (i.e., the horizontally sectional shape of the outer body is rectangular). In the case where the inner space is designed in a cylindrical shape, when the sample decomposing solution 8 stocked at the bottom portion of the container 1 is heated to be vaporized and convected, the sample decomposing vapor uniformly spreads over the inner space.

In this embodiment, the upper portion of the inner space S of the container 1, that is, a ceiling portion 10 of the lid body 2 is preferably designed in a curved shape such as a spherical shape or the like. Accordingly, even when the acidic components of the vaporized sample decomposing solution 8 or water are condensed and liquefied at the ceiling portion, the droplets of these components can be prevented from adhering to the ceiling portion by the curved shape of the ceiling portion 10, and promoted to flow down along the curved surface of the ceiling portion 10.

On the other hand, according to the conventional pressure vapor-phase decomposing method as described above, elution materials from PTFE, etc. which are constituent materials of the container may be contaminated into the condensed droplets which adhere to the ceiling portion of the container, and further these droplets may drop into the sample containers to lower the analysis precision. However, according to the treatment apparatus of the present invention, the contamination phenomenon as described above can be prevented, and the analysis of the impurities can be properly performed with high analysis precision. In this case, the droplets which flow down along the curved surface of the ceiling portion may be trapped on the step 5. However, if the analysis sample container 6 has a sufficiently high peripheral wall, no trouble occurs even when a small amount of droplets are trapped on the step 5.

Normally, the analysis sample container 6 is disposed on the step 5 while it is not closely engaged with the notch portion C, so that the trapped droplets can be made to flow out through the gap between the analysis sample container 6 and the notch portion C into the sample decomposing solution 8 at the bottom portion of the lower body 3. Further, if occasion demands, small grooves G may be suitably formed to extend from the step 5 to the notch portion C, whereby the droplets flowing down along the ceiling portion can be positively guided to the notch portion C side, passed over the lower side of the analysis sample container 6 and returned to the sample decomposing solution 8 at the bottom portion. The small grooves G may be formed on only the step 5 except for the notch portion C.

In the present invention, the lid body 2 and the lower body 3 of the container 1 are not necessarily required to divide the cylindrical body of the container 1 into equal two parts, and they may be designed so that the sample containers on the step and the sample decomposing solution are held while they are not brought into contact with each other and the container is kept to be hermetically sealed. For example, a flat-plate type lid body in which an opening portion is provided at the upper end portion thereof and the inner surface corresponding to the ceiling portion is designed in a spherical shape, may be disposed to keep the container in the hermetically sealed state. Further, each of the lid body 2, the lower body 3 and the ring-shaped analysis sample container of the treatment apparatus of the present invention is preferably constructed by a single body of PTFE having a suitable thickness which is sold in the market. Ordinarily, PTFE having a thickness of about 10 to 20 mm may be used.

Next, the analysis of the impurities in silicic material using the treatment apparatus thus constructed will be described. In order to perform the analysis, a predetermined amount of samples are set on the recessed sample mount portions 7 of the ring-shaped sample container 6, and then subjected to a vapor-phase decomposition treatment. In order to conduct the vapor-phase decomposition treatment, the sample decomposing solution (HF–HNO$_3$ solution) is stocked at the bottom portion and the container 1 is heated. The heating process is carried out so that the solution is vaporized, and like the prior art, the heating process is carried out at about 120° to 150° C.

The heating process of the container 1 may be performed by using a heating bath filled with a predetermined heating medium. Further, it may be performed while the container 1 is disposed on an iron plate having a heating means. By heating the container 1, the sample decomposing solution 8 stocked in the lower body 3 is vaporized, and HF–HNO$_3$ vapor is convected in the inner space S of the container. Therefore, the samples 9 are decomposed and sublimated, and dissolved into the sample decomposing solution 8. Finally, the impurities other than the silicic materials remain in the analysis sample mount portions 9. The residue is withdrawn to analyze the amount of the impurities in each sample with high precision by using an analysis method such as a flameless atomic absorption method or ICP-MS method (Inductively Coupled Plasma Mass Spectrometry) like the prior art.

Embodiment

A treatment apparatus comprising a cylindrical container 1 was formed of a single body of PTFE having a thickness of about 16 mm in the same manner as that shown in FIGS. 3 and 4, and the container 1 was disposed in a clean bench in a pre-treatment clean room (clean class 10) for semiconductor wafer silicon to perform a pre-treatment test for analyzing the impurities of semiconductor wafer silicon.

First, three silicon bulk samples of 1 g were respectively measured and put on each of alternate recess portions of six sample mount portions 7 of the ring-shaped analysis sample container 6, and no sample was put on the other recess portions. Subsequently, the sample decomposing solution was introduced into the lower body 3, and the ring-shaped analysis sample container 6 on which the samples were put at three positions was mounted on the notch portion C. Thereafter, the lid body 2 and the lower body 3 were engaged with each other at the screw portion 4 to seal the container 1 hermetically. The hermetically sealed container 1 was heated to about 150° C. by a hot plate and kept at that temperature for 20 hour. The sample decomposing solution (HF–HNO$_3$) was formed by mixing semiconductor reagents of hydrofluoric acid (50 wt %) and nitric acid (50 wt %) produced by Hirota Chemical Co., Ltd. into pure water to make a mixture of about 200 ml. The sample decomposing solution was vaporized by the heating, and the pressure in the sealed container 1 was estimated to be about 0.2 MPa measured by a pressure sensor.

Figure 8:
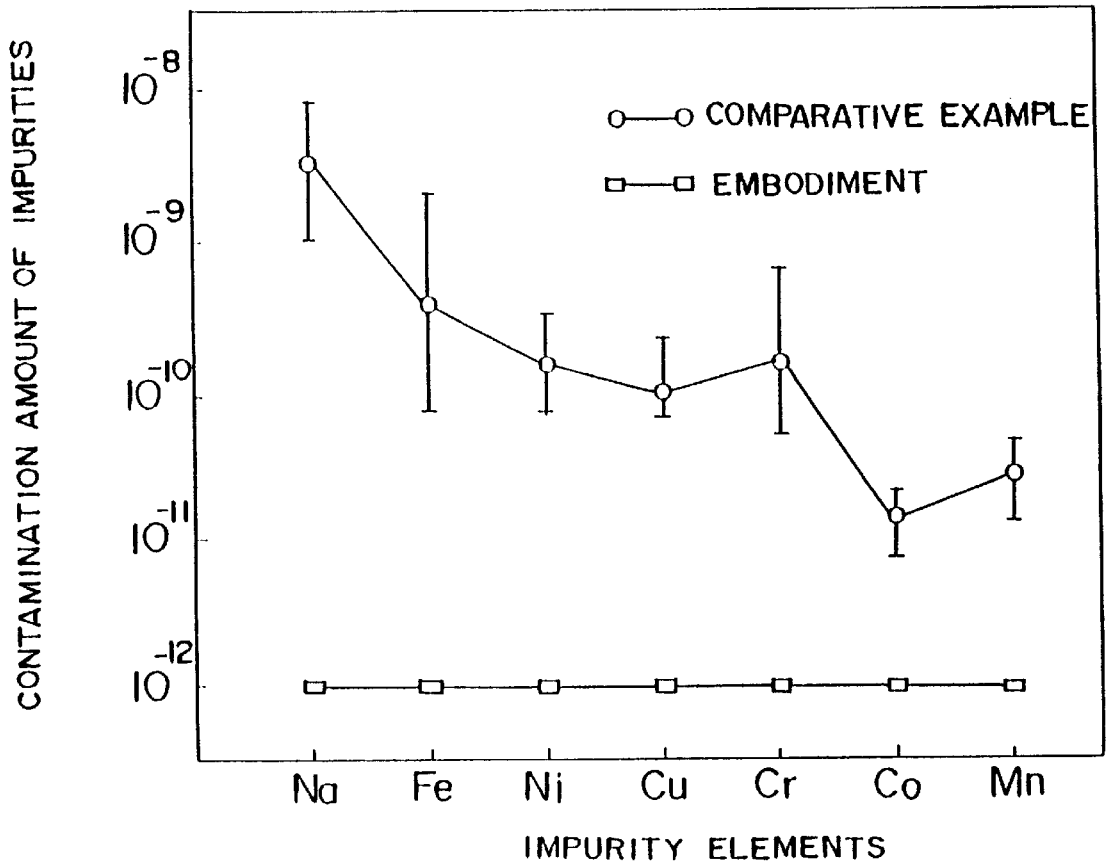
FIG. 8 is a graph showing a quantitative analysis result of impurity elements between an embodiment of the present invention and the comparative example, which shows the variation of the content of each of the impurity elements.

After heated, the container 1 was cooled to the room temperature and the lid body 2 is released. The silicon samples located at the three positions had been decomposed and sublimated. A minute amount of residues were withdrawn from each sample mount portion 7 and then subjected to an element analysis. The quantitative analysis of elements was performed while the samples were mounted and measured in an SPQ-8000A type mass treatment apparatus having an AT-300 type auto sampler and An EV-300 type heat-vaporizing apparatus (produced by Seiko electronics Co., Ltd.). The measurement was performed in a clean room (clean class 10$^3$). As a result, the content of the impurity elements which were withdrawn and analyzed from the three sample mount portions 3 on which no sample was put. FIG. 8 is a graph showing the amount of the impurities which invaded into the sample mount portions 7 during the vapor-phase decomposing and sublimating process.

The container and the ring-shaped analysis sample container as described above were constructed on the following condition. That is, the lid body was formed of a cylindrical body (100 mm in height, 126 mm in outer diameter and 92 mm in inner diameter) having one closed end portion and one open end portion. The closed one end portion of the lid body was designed in a spherical shape to have a radius of curvature of 46 mm, and the inner peripheral surface of the other open end portion was cut by 9 mm in thickness and 30 mm in length. The inner peripheral surface was threaded at a pitch of about 2 mm, and further the screw link surface was polished to have a surface roughness of 1.2 $\mu$m to form a screw portion 4. The lower body was formed of a cylindrical body (75 mm in height, 54 mm in outer diameter and 38 mm in inner diameter) having one closed end portion and one open end portion. The open end portion of the lower body was threaded to form a screw portion 4 which met the screw portion 4 of the lid body. Further, the inner peripheral surface of the lower body was cut by 8 mm in thickness and 5 mm in height to have a step 5 which met the abutment top face of the lid body. The surface of the step 5 was further cut from the inner peripheral surface by 2 mm in thickness and 5 mm in height to have a notch portion C. Further, small grooves G were formed at angular intervals of about 60 degrees so as to extend from the surface of the step 5 to the notch portion C, and recess portions of 18 mm in diameter and 26 mm in depth, each recess portion having a curved surface, were formed at angular intervals of about 60 degrees on the ring-shaped surface of the PTFE ring-shaped body (28 mm in thickness, 30 mm in inner diameter and 78 mm in outer diameter) to obtain the ring-shaped analysis sample container.

Comparative Example

Figure 1:
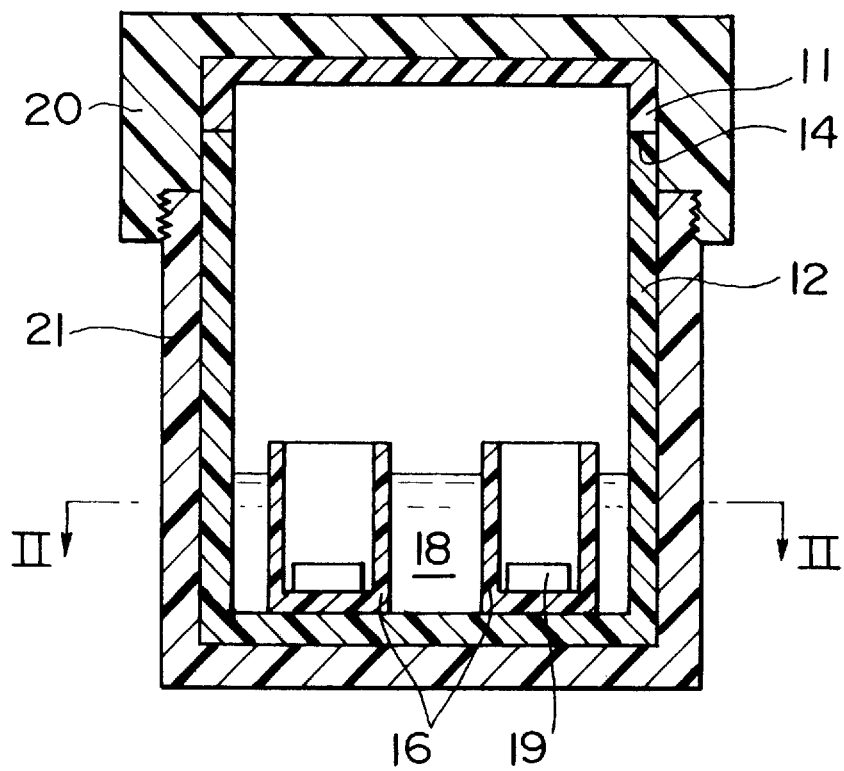
FIG. 1 is a longitudinal sectional view showing a conventional pressure vapor-phase decomposing treatment apparatus.
Figure 2:
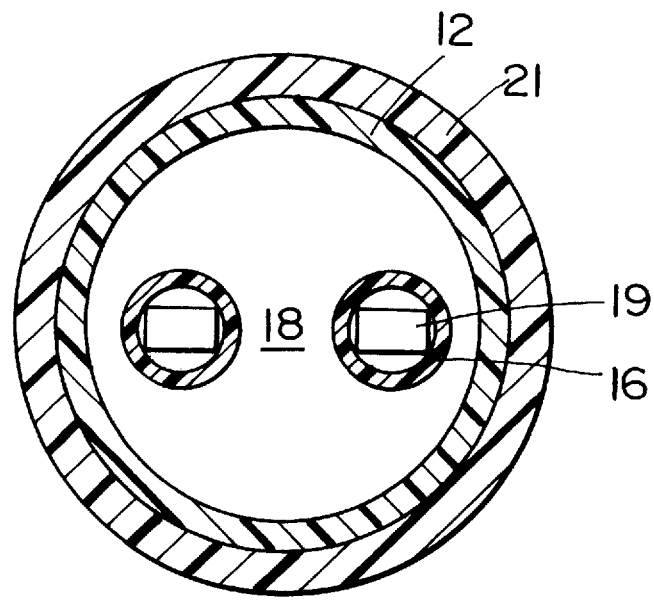
FIG. 2 is a cross-sectional view taken along a line II—II of FIG. 1.

The same treatment as the above-described embodiment was performed three times by using the conventional treatment apparatus shown in FIGS. 1 and 2 while the same silicon bulk sample as the embodiment was put in one of the sample mount containers 16 and no sample was put in the other sample mount containers. In any case, the silicon bulk sample vanished like the embodiment. The residues withdrawn from the sample mount containers 16 on which no sample was put were subjected to the same element analysis as the embodiment. FIG. 8 shows the element analysis result with dispersion ranges and average values (as indicated by circles in FIG. 8).

As is apparent from the embodiment and the comparative example, according to the impurity analysis using the treatment apparatus of the present invention, the contamination amount of the impurities is below 1 ppt and no dispersion was observed. On the other hand, according to the conventional analysis, the contamination amount of the impurities is large, and a large dispersion is observed. Therefore, even if an empty test (i.e., no sample is put on any sample mount container) is performed to correct analysis values, no proper corrected data could be obtained. That is, it is actually impossible to perform ppt-order analysis by using the conventional method. On the other hand, it is clearly apparatus that the quantitative analysis of impurities in ppt order can be performed according to the impurity analysis method of silicic materials by using the treatment apparatus of the present invention.

What is claimed is:

1. A treatment apparatus for analyzing the impurities in silicic material with high precision comprising:

(1) a container having at inner space in which at least one analysis sample container and a sample decomposing solution are accommodated;

(2) wherein said container is divided into a lid body having an inner space therein and a lower body having an inner space therein, each of said lid body and said lower body being opened at a division surface side thereof to have an open end portion and being closed at the surface side opposite to the division surface side to have a closed end portion thereof, the inner surface of the closed end portion of said lid body being formed in a concave shape to form a ceiling portion while the closed end portion of said lower body forms a bottom portion at which the sample decomposing solution can be stocked;

(3) wherein the inner peripheral surface of the open end portion of said lower body is formed in a stepwise shape so that said analysis sample container is disposed to be spaced from the surface of the decomposing solution which is stocked at the bottom portion, and the inner peripheral surfaces of said lid body and the lower body are smoothly continuously threadily engaged with each other through abutment faces thereof;

wherein each of the lid body and the lower body has, as an engagement means, an abutment face portion and a screw portion at the open end thereof, said abutment face portion having a surface roughness (Ra) of 0.1 to 3 μm, said screw portion having a thread pitch of 1 to 3 mm, a length of 10 to 70 mm and a flank portion thereof having a surface roughness (Ra) of 0.1 to 3 μm, and wherein the lid body and the lower body are threadily engaged with each other through engagement between the screw portions thereof, and the inner peripheral surface of the container at the abutment portion of the lid body and the lower body forms a smooth continuous surface, and wherein the container has such a sealing state that the inner space thereof can be kept at a pressure range of 0.01 to 0.500 MPa.

2. The treatment apparatus as claimed in claim 1, wherein the inner peripheral surface of the open end portion of the lower body is designed in a two-step structure, said analysis sample container being mounted on a lower step.

3. The treatment apparatus as claimed in claim 1, wherein the peripheral wall of the open end portion of said lid body is cut in a stepwise shape on the inner peripheral surface thereof to have a female screw portion and an abutment top face, and the peripheral wall of the open end portion of said lower body is cut to have a male screw portion and an abutment seat face, said lid body and said lower body being threadily engaged with each other through the engagement between the female and male screw portions.

4. The treatment apparatus as claimed in claim 1, wherein the peripheral wall of the open end portion of said lid body has a male screw portion and an abutment top face on the outer peripheral surface thereof, and the peripheral wall of the open end portion of said lower body has a female screw portion and an abutment seat face on the inner surface thereof, said lid body and said lower body are threadily engaged with each other through the engagement between the male and female screw portions.

5. The treatment apparatus as claimed in claim 1, wherein a female screw portion is concavely formed at an intermediate portion of the peripheral wall of the open end portion of said lid body, and a male screw portion is convexly formed at an intermediate portion of the peripheral wall of the open end portion of said lower body, said lid body and said lower body being threadily engaged with each other through the engagement between the female and male screw portions.

6. The treatment apparatus as claimed in claim 1, wherein a male screw portion is convexly formed at the intermediate portion of the peripheral wall of the open end portion of the lid body while a female screw portion is concavely formed at the intermediate portion of the peripheral wall of the open end portion of said lower body, said lid body and said lower body being threadily engaged with each other through the engagement between the male and female screw portions.

7. The treatment apparatus as claimed in claim 1, wherein said analysis sample container is designed in a ring shape and plural recess portions are formed in a ring portion of said analysis sample container so that samples are set in said recess portions.

8. The treatment apparatus as claimed in claim 7, wherein the inner bottom portion of each recess portion is designed to have a curved surface.

9. The treatment apparatus as claimed in claim 7, wherein said ring portion is formed of a thick member, and said recess portions are formed by boring holes in said ring portion.

10. The treatment apparatus as claimed in claim 1, wherein each of said lid body, said lower body and said analysis sample container comprises an unit body of polytetrafluoroethylene.

11. The treatment apparatus as claimed in claim 1, wherein the inner space of said container has a circular cross-sectional shape, and said analysis sample container has a ring-shaped body.

12. A method for analyzing the impurities in silicic material by placing the silicic material in the at least one analysis sample container of the treatment apparatus as claimed in claim 1, heating the apparatus, withdrawing residue remaining in the at least one analysis sample container and determining the amount and type of impurities in the residue.

13. A semiconductor manufacturing process for regularly analyzing the impurities of silicic materials for a semiconductor manufacturing process comprising placing the silicic material in the at least one analysis sample container of the treatment apparatus as claimed in claim 1, heating the apparatus, withdrawing residue remaining in the at least one analysis sample container and determining the amount and type of impurities in the residue.

* * * * *